(12) United States Patent
Hammer et al.

(10) Patent No.: US 12,144,684 B2
(45) Date of Patent: Nov. 19, 2024

(54) CHARACTERIZING SOFT TISSUE SUBRUPTURE DAMAGE AND INCOMPLETE TEAR DAMAGE FOR PERFORMING A PROCESS

(71) Applicant: The Boeing Company, Chicago, IL (US)

(72) Inventors: Liisa Charlie Hammer, Seattle, WA (US); Karen Chiyono Takatani, Renton, WA (US); James Dean Cotton, Issaquah, WA (US); Richard Jay Gardner, Brier, WA (US)

(73) Assignee: THE BOEING COMPANY, Arlington, VA (US)

( * ) Notice: Subject to any disclaimer, the term of this patent is extended or adjusted under 35 U.S.C. 154(b) by 443 days.

(21) Appl. No.: 17/464,379

(22) Filed: Sep. 1, 2021

(65) Prior Publication Data

US 2023/0067316 A1   Mar. 2, 2023

(51) Int. Cl.
*A61B 8/08* (2006.01)
*A61B 5/055* (2006.01)

(52) U.S. Cl.
CPC .............. *A61B 8/485* (2013.01); *A61B 5/055* (2013.01)

(58) Field of Classification Search
None
See application file for complete search history.

(56) References Cited

U.S. PATENT DOCUMENTS

| 9,610,036 B1 | 4/2017 | De Sapio et al. |
| 2003/0135129 A1 | 7/2003 | Cusimano et al. |

(Continued)

FOREIGN PATENT DOCUMENTS

| EP | 2839772 A1 | 2/2015 |
| JP | 2011141706 A | 7/2011 |

(Continued)

OTHER PUBLICATIONS

Crisan, Carmen-Clara (PCT Authorized Officer), Notification of Transmittal of the International Search Report and the Written Opinion of the International Searching Authority, or the Declaration, mailed Jul. 19, 2022, for International Application No. PCT/US2022/022473, 22 pages.

(Continued)

*Primary Examiner* — Walter L Lindsay, Jr.
*Assistant Examiner* — Geoffrey T Evans
(74) *Attorney, Agent, or Firm* — MH2 Technology Law Group LLP

(57) ABSTRACT

Disclosed techniques for performing a process can include performing, by a plurality of subjects, a first repetitive movement with a specified stress or strain per cycle; analyzing for soft tissue disorganization or partially torn soft tissue in each of the plurality of subjects; generating an association relating stress or strain to a number of cycles that cause a transition to subrupture damaged tissue or to incomplete tear damaged tissue; measuring a stress or strain per cycle for a second repetitive movement that makes up the process; determining a limit on a number of cycles of the second repetitive movement intended to avoid at least one of: a transition to subrupture damaged soft tissue or to incomplete tear damage tissue; and performing the second repetitive movement as part of the process while ensuring that no individual subject exceeds the limit on the number of cycles of the second repetitive movement.

20 Claims, 5 Drawing Sheets

(56) References Cited

U.S. PATENT DOCUMENTS

| | | |
|---|---|---|
| 2017/0055836 A1 | 3/2017 | Thelen et al. |
| 2021/0174929 A1 | 6/2021 | Bruchal et al. |
| 2022/0192637 A1 | 6/2022 | Kirby et al. |
| 2022/0230732 A1 | 7/2022 | Hammer et al. |
| 2022/0338928 A1 | 10/2022 | Hammer et al. |

FOREIGN PATENT DOCUMENTS

| | | |
|---|---|---|
| WO | 2014201020 A1 | 12/2014 |
| WO | 2021113725 A1 | 6/2021 |

OTHER PUBLICATIONS

Huber, G., et al., "Dependence of spinal segment mechanics on age and posture," Research Project F 2069—Bundesanstalt für Arbeitsschutz und Arbeitsmedizin, May 3, 2010, pp. 1-173.

Qasim, M., et al., "Initiation and progression of mechanical damage in the intervertebral disc under cyclic loading using continuum damage mechanics methodology: A finite element study," Journal of Biomechanics, vol. 45, No. 11, Jul. 26, 2012 (Published online Jun. 8, 2012), pp. 1934-1940.

Weiss, J.A., et al., "Three-dimensional finite element modeling of ligaments: Technical aspects," Medical Engineering & Physics, vol. 27, No. 10, Aug. 8, 2005, pp. 845-861.

Zhang, Q., et al., "Techniques for In Vivo Measurement of Ligament and Tendon Strain: A Review," Annals of Biomedical Engineering, vol. 49, No. 1, Jan. 2021 (Published online Oct. 6, 2020), pp. 7-28.

Tse, K.M., et al., "A review of head injury and finite element head models," American Journal of Engineering, Technology and Society, vol. 1, No. 5, Dec. 2014, pp. 28-52.

Doherty, F. (PCT Authorized Officer), Notification Concerning Transmittal of International Preliminary Report on Patentability and Written Opinion of the International Searching Authority mailed Nov. 9, 2023, for International Application No. PCT/US2022/022473, 15 pages.

Buckley, M.R., et al., "Validation of an Empirical Damage Model for Aging and In Vivo Injury of the Murine Patellar Tendon," Journal of Biomechanical Engineering, vol. 135, Apr. 2013, pp. 041005-1-041005-7.

Colombini, D., et al., "Preventing upper limb work-related musculoskeletal disorders (UL-WMSDS): New approaches in job (re)design and current trends in standardization," Applied Ergonomics, vol. 37, No. 4, Jul. 2006, pp. 441-450.

Fung, D.T., et al., "Subrupture Tendon Fatigue Damage," Journal of Orthopaedic Research, vol. 27, Feb. 2009 (Published online Aug. 6, 2008), pp. 264-273.

Takatani, K.C., et al., "A new approach to prevent overuse injuries of the rotator cuff supraspinatus tendon using the cumulative fatigue concept," Theoretical Issues in Ergonomics Science, vol. 18, No. 5, 2017 (Published online Jun. 22, 2017), pp. 455-476.

Van Eerd, D., et al., "Effectiveness of workplace interventions in the prevention of upper extremity musculoskeletal disorders and symptoms: an update of the evidence," Occup. Environ. Med., vol. 73, 2016 (Published Online First Nov. 9, 2015), pp. 62-70.

Lake et al., "Effect of Fiber Distribution and Realignment on the Nonlinear and Inhomogeneous Mechanical Properties of Human Supraspinatus Tendon Under Longitudinal Tensile Loading," NIH Public Access Author Manuscript, J. Orthop Res. Dec. 2009; 27 (12), 1596, 17 pages.

Qasim et al., "Initiation and Progression of Mechanical Damage in the Intervertebral Disc Under Cyclic Loading Using Continuum Damage Mechanics Methodology: A Finite Element Study," Journal of Biomechanics 45 (2012) 1934-1940.

Rabello et al., "Substantiating the Use of Ultrasound Tissue Characterization in the Analysis of Tendon Structure: A Systematic Review," www.cjsportmed.com, vol. 31, No. 3, May 2021.

Schechtman et al., "In Vitro Fatigue of Human Tendons," J. Biometchanics, vol. 30, No. 8, pp. 829-839, 1997.

Van Schie et al., "Ultrasonographic Tissue Characterisation of Human Achille Tendons: Quantification of Tendon Structure Through a Novel Non-Invasive Approach," Br. J. Sports Med, 2010, 44, 1153-1159.

Kim et al., "In Vivo Strain Analysis of the Intact Supraspinatus Tendon by Ultrasound Speckles Tracking Imaging," Journal of Othopaedic Research, Dec. 2011, 1931-1937.

Klauser et al., "Sonoelastography: Musculoskeletal Applications," Radiology: vol. 272, No. 3, Sep. 2014, 622-633.

Prado-Costa et al, "Ultrasound elastography: compression elastography and shear-wave elastography in the assessment of tendon injury," Insights into Imaging (2018) 9:791-814.

Van Schie et al., "Efficacy of computerized discrimination between structure-related and non-structure-related echoes in ultrasonographic images for the quantitative evaluation of the structural integrity of superficial digital flexor tendons in horses," AJVR, vol. 62, No. 7, Jul. 2001, 1159-1166.

Extended European Search Report for European Application No. 21215965.1 dated Jun. 8, 2022 (11 pages).

De Sapio, V., et al., "Demographic Specific Musculoskeletal Models of Factory Worker Performance, Fatigue, and Injury," 2016 IEEE Aerospace Conference, IEEE, Mar. 5, 2016, pp. 1-13.

Golze, Doreen (PCT Authorized Officer), Notification of Transmittal of the International Search Report and the Written Opinion of the International Searching Authority (Forms PCT/ISA/220, PCT/ISA/210 and PCT/ISA/237) for International Application No. PCT/US2020/063430 dated Mar. 26, 2021 (15 pages).

Lindner, Nora (PCT Authorized Officer), Notification Concerning Transmittal of International Preliminary Report on Patentability (Form PCT/IB/373) for International Application No. PCT/US2020/063430 dated Jun. 16, 2022 (8 pages).

Office Action mailed in CA 3,158,278 on Feb. 19, 2024. (5 Pages).

Daneshmandi, H., et al., "An ergonomic intervention to relieve musculoskeletal symptoms of assembly line workers at an electronic parts manufacturer in Iran," Work, vol. 61, 2018, pp. 515-521.

Shikatani (JP Examiner), Office Action issued on Jun. 25, 2024, for Japanese Application No. 2022-534139, including English machine translation, 8 pages.

Garg, A., "Applications of biomechanics for prevention of work-related musculoskeletal disorders," Ergonomics, vol. 52, No. 1, Jan. 2009, pp. 36-59.

Vassell, Meredith Abbott (Examiner), Final Office Action issued Sep. 25, 2024 in related U.S. Appl. No. 17/110,953 filed Dec. 3, 2020, 29 pages.

CHARACTERIZING SOFT TISSUE SUBRUPTURE DAMAGE AND INCOMPLETE TEAR DAMAGE FOR PERFORMING A PROCESS

FIELD

The subject matter described herein generally relates to ergonomics and industrial hygiene. More particularly, the subject matter disclosed herein relates to characterizing soft tissue for mitigating or reducing soft tissue repetitive stress injuries in performing a process.

BACKGROUND

Overuse, or ergonomics, injuries are some of the most significant of workplace injuries. Accordingly, there is a need to understand the dynamics of workplace or other activities that contribute to and can result in stress, for example to a tendon, to address a task or cycle of tasks that contribute to an injury.

Existing ergonomic analysis and recommendations typically rely on theoretical constructs based on over-simplified characterizations of soft tissue such as a joint complex. These can rely on psychophysical estimates of acceptable exertion levels or a generalization of the forces on the joint from a single moment load about a point. The existing approaches give only limited estimates of risk and are of limited use in practice.

Moreover, medical, therapeutic, and pharmacological research is dedicated to (or focuses on) individuals after injury has occurred: surgical procedures, physical therapy regimens, and treatments to speed recovery. Injury detection is focused on after a patient has self-reported an injury, not on screening for risk prior to injury. While traditional ergonomics practices seek to prevent injuries, it has only or so far been done at the macro level with epidemiological methods: based on estimated work exposure, create an estimate of when a person will self-report an injury based on discomfort level or pain, and create guidelines below that threshold, and most injuries are defined by generalized body area: the entire shoulder, knee, or back, rather than individual components.

SUMMARY

This disclosure comprises examples according to the following Clauses.

Clause 1: A method of performing a process, the method comprising: performing, by a plurality of subjects, a first repetitive movement with at least one of a specified stress per cycle or a specified strain per cycle; analyzing for a presence of at least one of soft tissue disorganization or partially torn soft tissue in each of the plurality of subjects; generating an association, based on the analyzing, wherein the association relates one of stress or strain to a number of cycles that cause at least one of: a transition to subrupture damaged tissue, or a transition to incomplete tear damaged tissue; measuring at least one of a stress per cycle or a strain per cycle for a second repetitive movement comprising the process; determining, based on the association, a limit on a number of cycles of the second repetitive movement intended to avoid at least one of: a transition to subrupture damaged soft tissue, or a transition to incomplete tear damage tissue; and performing the second repetitive movement as part of the process, wherein the performing the second repetitive movement comprises ensuring that no individual exceeds the limit on the number of cycles of the second repetitive movement.

Clause 2: The method of Clause 1, wherein the analyzing comprises analyzing using at least one non-invasive technique.

Clause 3: The method of any of Clauses 1 or 2, wherein the at least one non-invasive technique comprises at least one of: ultrasound speckle tracking imaging, ultrasound compression elastography, ultrasound strain elastography, shear wave elastography, magnetic resonance imaging, ultrasound tissue characterization, or a combination thereof.

Clause 4: The method of any of Clauses 1, 2, or 3, wherein the association relates one of stress or strain to a number of cycles that cause a transition to subrupture damaged soft tissue.

Clause 5: The method of any of Clauses 1-4, wherein the association relates one of stress or strain to a number of cycles that cause a transition to incomplete tear damaged tissue.

Clause 6: The method of any of Clauses 1-5, further comprising: repeating, for each of a plurality of loading conditions, the performing the first repetitive movement, the analyzing, and the generating, wherein the plurality of loading conditions comprise at least two of: compression, shear, or tension, and wherein a plurality of associations comprising the association are produced; and determining a loading condition for the second repetitive movement; wherein the association corresponds to the loading condition for the second repetitive movement.

Clause 7: The method of any of Clauses 1-6, wherein the association comprises a curve relating one of a stress or strain on a first axis to a number of cycles on a second axis.

Clause 8: The method of any of Clauses 1-7, wherein the process comprises a manufacturing process.

Clause 9: The method of any of Clauses 1-8, wherein the determining the limit on the number of cycles of the second repetitive movement is further based on healing data for the soft tissue and at least one recovery period.

Clause 10: The method of any of Clauses 1-9, wherein the healing data comprises data representing a difference in levels of soft tissue disorganization between a first soft tissue in a first subject measured using an invasive technique and a second soft tissue in a second subject measured using a non-invasive technique.

Clause 11: A system for performing a process, the system comprising at least one electronic processor that executes instructions to perform operations comprising: generating an association, based on analyzing for a presence of at least one of soft tissue disorganization or partially torn soft tissue in each of a plurality of subjects that perform a first repetitive movement with at least one of a specified stress per cycle or a specified strain per cycle, wherein the association relates one of stress or strain to a number of cycles that cause at least one of: a transition to subrupture damaged tissue, or a transition to incomplete tear damaged tissue; and determining, based on the association and a measurement of at least one of a stress per cycle or a strain per cycle for a second repetitive movement comprising the process, a limit on a number of cycles of the second repetitive movement intended to avoid at least one of: a transition to subrupture damaged soft tissue, or a transition to incomplete tear damage tissue; wherein the second repetitive movement is performed as part of the process while ensuring that no individual exceeds the limit on the number of cycles of the second repetitive movement.

Clause 12: The system of Clause 11, wherein the generating the association is further based on analyzing for a presence of at least one of soft tissue disorganization or partially torn soft tissue using at least one non-invasive technique.

Clause 13: The system of any of Clauses 11 or 12, wherein the at least one non-invasive technique comprises at least one of: ultrasound speckle tracking imaging, ultrasound compression elastography, ultrasound strain elastography, shear wave elastography, magnetic resonance imaging, ultrasound tissue characterization, or a combination thereof.

Clause 14: The system of any of Clauses 11, 12, or 13, wherein the association relates one of stress or strain to a number of cycles that cause a transition to subrupture damaged soft tissue.

Clause 15: The system of any of Clauses 11-14, wherein the association relates one of stress or strain to a number of cycles that cause a transition to incomplete tear damaged tissue.

Clause 16: The system of any of Clauses 11-15, wherein the operations further comprise: repeating, for each of a plurality of loading conditions, the generating and the determining, wherein the plurality of loading conditions comprise at least two of: compression, shear, or tension, and wherein a plurality of associations comprising the association are produced; and obtaining a loading condition for the second repetitive movement; wherein the association corresponds to the loading condition for the second repetitive movement.

Clause 17: The system of any of Clauses 11-16, wherein the association comprises a curve relating one of a stress or strain on a first axis to a number of cycles on a second axis.

Clause 18: The system of any of Clauses 11-17, wherein the process comprises a manufacturing process.

Clause 19: The system of any of Clauses 11-18, wherein the limit on the number of cycles of the second repetitive movement is further based on healing data for the soft tissue and at least one recovery period.

Clause 20: The system of any of Clauses 11-19, wherein the healing data comprises data representing a difference in levels of soft tissue disorganization between a first soft tissue in a first subject measured using an invasive technique and a second soft tissue in a second subject measured using a non-invasive technique.

DRAWINGS

The above and/or other aspects and advantages will become more apparent and more readily appreciated from the following detailed description of examples, taken in conjunction with the accompanying drawings, in which.

DETAILED DESCRIPTION

Figure 1:
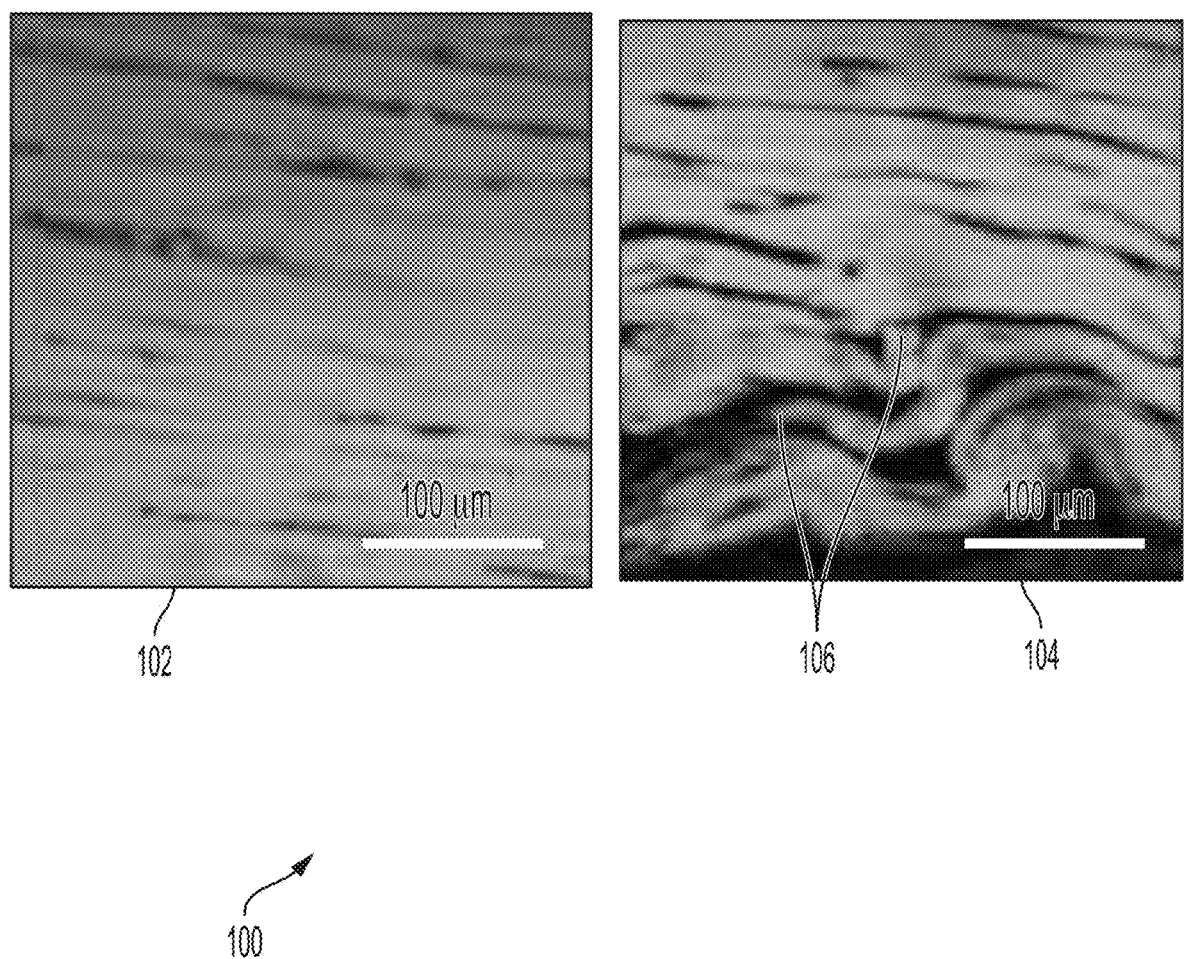
FIG. 1 depicts images of undamaged and subrupture damaged soft tissue.

Exemplary aspects will now be described more fully with reference to the accompanying drawings. Examples of the disclosure, however, can be embodied in many different forms and should not be construed as being limited to the examples set forth herein. Rather, these examples are provided so that this disclosure will be thorough and complete, and will fully convey the scope to those skilled in the art. In the drawings, some details may be simplified and/or may be drawn to facilitate understanding rather than to maintain strict structural accuracy, detail, and/or scale.

Studies linking, for example, shoulder pain or rotator cuff injuries to workplace factors have identified overhead work (defined as elbows above shoulders), applied force, repetitive motion, and physical loads as significant contributors. However, the quality of these studies varies, and evidence did not consistently demonstrate a significant dose-response relationship.

As a result, current published guidelines for injury risk are insufficient for use in occupational ergonomics injury prevention programs. Existing guidelines are insufficient because they are based on previous workplace studies that focused on self-reported pain and discomfort, which typically occurs only after injury (e.g., complete tear) has been sustained. They are further inadequate because they do not provide clear, acceptable limits for shoulder-based work activity in a workplace and they do not account for the interaction of posture, force, cycles, duration, and vibration. Instead, existing guidelines regarding shoulder injuries recommend reduction or elimination of overhead or extended shoulder postures. Practitioners are faced with degrees of unknown risk. Such unknown risk limits the solutions space for effective interventions.

While eliminating repetitive, awkward, or taxing shoulder use is infeasible in some industries, damage from these actions can be mitigated. Without sufficient risk thresholds, the question persists as to what degree risk factors (e.g., force, vibration, posture, repetition, duration, and combinations thereof) should be reduced to mitigate or prevent injury. The question is further complicated because this type of work can involve many repetitive motions (e.g., painting) and/or forces (e.g., drilling) and/or loads (e.g., welding). Guidelines according to some examples may therefore take into account risk factor interaction and work/rest cycles.

Given the inability of establishing causality with epidemiological data alone, an alternative approach is needed. The models, detection techniques, and related aspects disclosed herein bridge many of the gaps that traditional epidemiological studies have not been able to close.

The present disclosure relates to methods, systems, and computer readable media for performing a process, such as a manufacturing process, while ameliorating injury. The methods, systems, and computer readable media may be used to generate one or more models for determining and predicting various levels of soft tissue damage.

The models can be based on the existence of multiple damage regimes for the soft tissue. For example, a first damage regime, the "no damage regime", may represent that the soft tissue is undamaged. Transition out of the first damage regime may occur when the soft tissue sustains subrupture damage, e.g., soft tissue disorganization, microtears and/or overextension, but no macroscopically detectable tearing of the tendon tissue. A second damage regime, the "subrupture damage regime", may represent that the soft tissue may have sustained damage up to and including subrupture damage, but no macroscopic tears. Transition out of the second damage may occur when the soft tissue sustains a macroscopic tear, but not a full tear. A third damage regime, the "incomplete tear damage regime", may represent that the soft tissue may have sustained damage up to and including a macroscopic tear, but has not fully torn. Transaction out of the third damage regime may occur when the soft tissue fully tears (or significantly tears, e.g., greater than 50% torn). In some applications, the models may be used to address ergonomic issues related to a task to inform and establish guidelines to prevent or otherwise mitigate an injury.

Examples provided herein may utilize a variety of techniques to characterize the various damage regimes their transitions. Such techniques may be used to detect a transition out of a damage regime. Each regime transition can then be correlated with a number of cycles of a movement and a corresponding stress (or strain) per cycle that is likely to cause the transition. Thus, each damage regime may be associated with a curve relating a stress (or strain) per cycle and a number of cycles to a transition out of the damage regime.

The techniques used to characterize the various damage regimes may be invasive or non-invasive and may be applied to a living human subject, a cadaver subject, a living animal subject, or a deceased animal subject. Example non-invasive techniques include ultrasound speckle tracking imaging, ultrasound compression elastography, ultrasound strain elastography, shear wave elastography, and ultrasound tissue characterization. Each subject can undergo a known number of cycles at a known stress (or strain) and may then be examined using one or more such techniques for signs of a transition out of the damage regime. If no transition is detected, the process can be repeated for additional increments of cycles, until a transition is detected. This process collects data that may then be used to generate a curve for each damage regime relating a number of cycles of a movement and a corresponding stress (or strain) per cycle to a transition out of the damage regime. The curves can then be used in a predicative manner to determine guidelines intended to prevent or mitigate injuries incurred while performing a process, such as a repetitive manufacturing process.

The techniques and related aspects disclosed herein can be applied to essentially any soft tissue, such as intervertebral (spinal) discs, ligaments, cartilage, tendons, and tendon systems. For example, essentially any tendon can be evaluated as part of the techniques disclosed herein. The tendon may include a mammalian tendon, such as a human tendon. Example tendons include: a teres minor tendon, an infraspinatus tendon, a supraspinatus tendon, a subscapularis tendon, a deltoid tendons, a biceps tendon, a triceps tendon, a brachioradialis tendon, a supinator tendon, a flexor carpi radialis tendon, a flexor carpi ulnaris tendon, an extensor carpi radialis tendon, an extensor carpi radialis brevis tendon, an iliopsoas tendon, an obturator internus tendon, an adductor longus tendon, an adductor brevis tendon, an adductor magnus tendon, a gluteus maximus tendon, a gluteus medius tendon, a quadriceps tendon, a patellar tendon, a hamstring tendon, a sartorius tendon, a gastrocnemius tendon, an Achilles tendon, a soleus tendon, a tibialis anterior tendon, a peroneus longus tendon, a flexor digitorum longus tendon, an interosseus tendon, a flexor digitorum profundus tendon, an abductor digiti minimi tendon, an opponens pollicis tendon, a flexor pollicis longus tendon, an extensor tendon, an abductor pollicis tendon, a flexor hallucis longus tendon, a flexor digitorum brevis tendon, a lumbrical tendon, an abductor hallucis tendon, a flexor digitorum longus tendon, an abductor digiti minimi tendon, an ocular tendon, a levator palpebrae tendon, a masseter tendon, a temporalis tendon, a trapezius tendon, a sternocleidomastoid tendon, a semispinalis capitis tendon, a splenius capitis tendon, a mylohyoid tendon, a thyrohyoid tendon, a sternohyoid tendon, a rectus abdominis tendon, an external oblique tendon, a transversus abdominis tendon, a latissimus dorsi tendon, an erector spinae tendon, and a combination thereof. Thus, examples may be used to develop models and generate injury amelioration guidelines for any activity, any soft tissue, involving any part of the body.

The results of the modeling allows for determination of criteria that can be used to develop guidelines to structure activities in a way so that subjects are not exposed to overuse that could otherwise lead to injury if not mitigated. The models can be used to set exposure limits and create usable work/rest cycles to predict and prevent overuse injuries, leading to a significant change in current approaches to ameliorating and reducing injuries. This allows for analysis and end results that were not previously done (and could not be done with existing knowledge or models). Examples disclosed herein are advantageous for heavy industry, especially where overhead work, cycles, and force exist, and for sports. Examples can be used to redesign work practices exceeding reasonable tendon strain or stress thresholds, create work-rest cycles based on soft tissue damage and repair rates, identify individuals for whom the model is not conservative, and implement strength training to improve tendon material properties.

In sum, there is a need to analyze and determine what factors lead to musculoskeletal soft tissue injuries. In particular, there is a need to determine parameters that are used to develop the damage models disclosed here. As described in detail herein, various invasive and non-invasive techniques may be used to obtain such parameters. The obtained parameters may be used in models that utilize multiple damage regimes. The damage regimes may account for damage short of a complete or near-complete tear. The models may then be used to improve ergonomics or develop new processes to help reduce or mitigate injury in performing a process. These and other techniques are described in detail below.

FIG. 1 depicts images 100 of undamaged soft tissue 102 and subrupture damaged soft tissue 104. Images 100 are of rat flexor digitorum longus tendons. As shown in FIG. 1, undamaged soft tissue 102 appears organized and aligned. By contrast, subrupture damaged soft tissue 104 is disorganized, showing bunches, clumps, and irregularities in alignment, e.g., of tendon fibers. Note that subrupture damaged tissue 104 does not display any significant tears, although it does appear to have a minor tear 106 of width slightly less than 20 µm. Images 100 were obtained using invasive techniques, e.g., dissection.

Some examples correlate an onset of subrupture damage with known numbers of cycles at specified stress (or strain) levels. Such an onset may represent a transition from a no damage regime to a subrupture damage regime. Examples that utilize a no damage regime and a subrupture damage regime are particularly beneficial, because typically no damage and subrupture damage produce no symptoms in a subject and may therefore lead to symptomatic incomplete tears.

Figure 2:
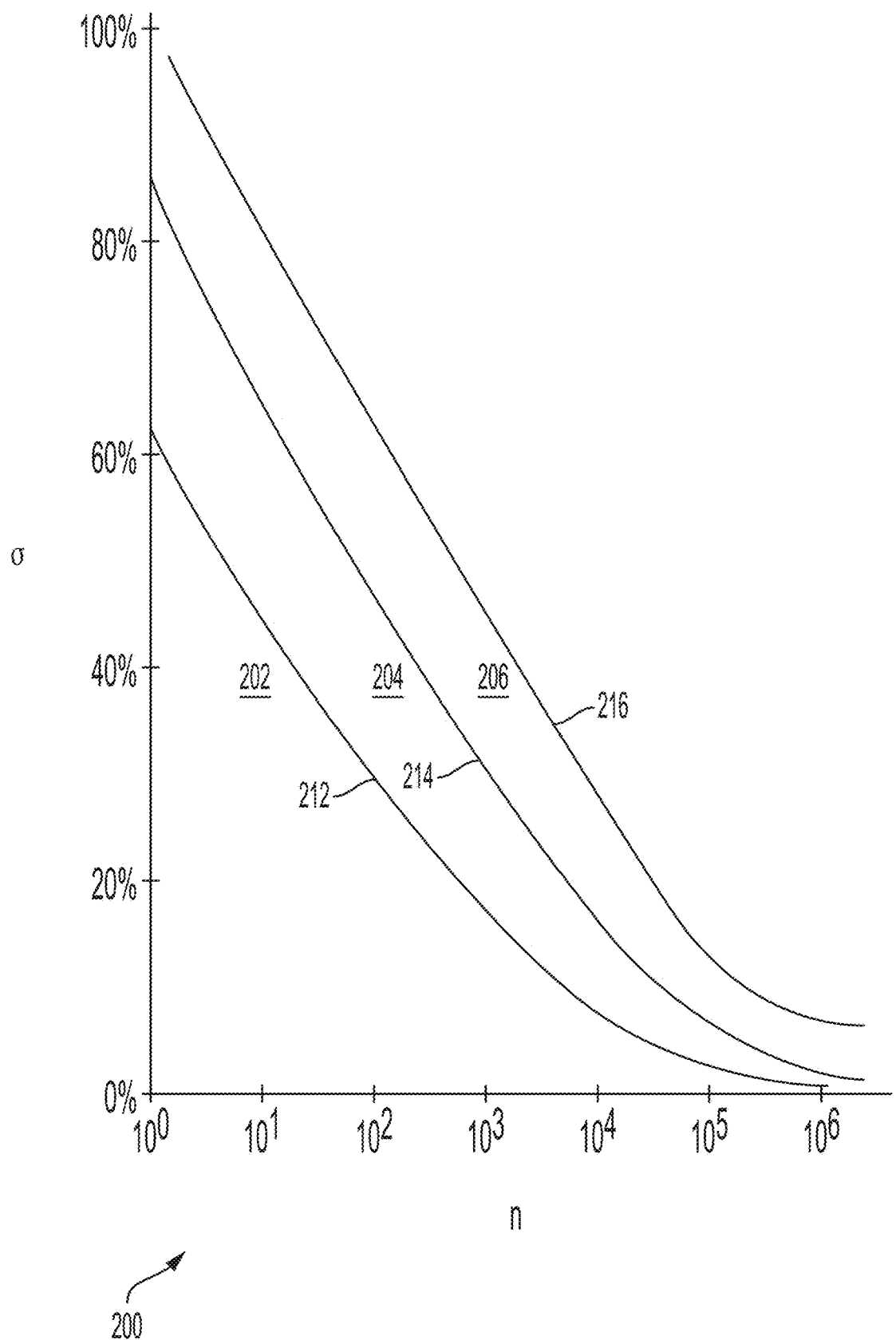
FIG. 2 is a chart depicting three damage regimes as functions of stress and number of cycles according to various examples.

FIG. 2 is a chart 200 depicting three damage regimes 202, 204, 206 as functions of stress and number of cycles according to various examples. In particular, chart 200 depicts no damage regime 202, subrupture damage regime 204, and incomplete tear damage regime 206. The x-axis of chart 200 represents number of cycles non a logarithmic scale, and the y-axis represents stress a, e.g., resultant stress, in terms of percentage of ultimate tensile strength (% UTS) on a linear scale. (According to some examples, the y-axis may represent strain in place of stress.) Transition curves 212, 214, and 216 represent numbers of cycles (x-axis) at specified stress levels (y-axis) to transition out of a respective regime when starting from undamaged soft tissue. For example, transition curve 212 represents cycles and stress levels for undamaged soft tissue to transition out of no damage regime 202, transition curve 214 represents cycles and stress levels for undamaged soft tissue to transition out of subrupture damage regime 204, and transition curve 216 represents cycles and stress levels for undamaged tissue to transition out of incomplete tear damage regime 206. Alternately, the transition curves 212, 214, and 216 may relate cycles at strain levels for the respective transitions.

No damage regime 202 represents healthy undamaged tissue. Transition out of no damage regime 202 may represent that the soft tissue has sustained subrupture damage, but not necessarily any significant tears. Thus, transition out of no damage regime 202 may represent that the soft tissue has sustained detectable damage. According to some examples, such detectable damage may be in the form of soft tissue disorganization. Various techniques for detecting subrupture damage (e.g., tendon fiber disorganization) indicative of transition out of no damage regime 202 are presented herein, e.g., in reference to FIG. 3.

According to some examples, transition out of no damage regime 202 does not require the presence of damage beyond detectable soft tissue disorganization, e.g., tears may not be required. According to various examples, transition out of no damage regime 202 occurs when the soft tissue has sustained disorganization and/or minor tears. Thus, according to some examples, transition out of no damage regime 202 occurs when the soft tissue sustains collegian disorganization and/or at least one tear that is longer than a predetermined length in the direction of the tear. Some examples may transition out of no damage regime 202 in the presence of soft tissue disorganization and/or the presence of at least one tear of greater than, by way of non-limiting examples, 20 μm, 50 μm, or 100 μm in the direction of the tear.

Subrupture damage regime 204 represents healthy undamaged tissue and subrupture damaged tissue. Transition out of subrupture damage regime 204 may represent that the soft tissue has sustained incomplete tear damage, but has not necessarily failed, e.g., completely torn. Thus, transition out of subrupture damage regime 204 may represent that the soft tissue has sustained at least one tear longer than a specified length in the direction of the tear. Techniques for detecting such tears indicative of a transition out of subrupture damage regime 204 are presented herein, e.g., in reference to FIG. 3.

According to some examples, transition out of subrupture damage regime 204 does not require the presence of damage beyond tears that exceed a specified length. According to some examples, transition out of subrupture damage regime 204 occurs in the presence of a tear of at least, e.g., 50 μm, 100 μm, 150 μm, or 200 μm, in the direction of the tear.

Incomplete tear damage regime 206 represents healthy undamaged tissue, subrupture damaged tissue, and incomplete tear damaged tissue. Incomplete tear damage regime 206 may represent damage accumulation in the form of a growing tear or fissure, cellular matrix damage or other biological damage. In particular, incomplete tear damage regime 206 may represent that a tear is present and may propagate (e.g., increase in length) in the soft tissue upon further usage. Transition out of incomplete tear regime 206 may represent that the soft tissue has failed, e.g., is no longer usable, or is no longer usable without significant pain.

According to some examples, transition out of incomplete tear damage regime 204 may represent that the soft tissue has sustained at least one tear of at least a certain size. According to some examples, transition out of incomplete tear damage regime 206 is indicated by a presence of tears of length over, e.g., 0.5 mm, 1 mm, 2 mm, or 5 mm in the direction of the tear. According to some examples, transition out of incomplete tear regime 206 is indicated by a presence of a tear that is over 1% of the width of the tendon, over 5% of the width of the tendon, or over 50% of the width of the tendon. Complete tear of, e.g., 100%, of the width of the tendon, is indicative of transition out of incomplete tear regime 206. Various techniques for detecting tears indicative of a transition out of incomplete tear damage regime 206 are presented herein, e.g., in reference to FIG. 3.

Each damage regime is cumulative and therefore includes prior damage from prior damage regime(s). Because damage is cumulative and damage regimes 202, 204, and 206 may start with undamaged tissue, damage regimes 202, 204, and 206 may occur sequentially. For example, because transition curve 214 represents cycles and stress levels for undamaged soft tissue to transition out of subrupture damage regime 204, a given soft tissue may pass through no damage regime 202 and subrupture damage regime 214 before transitioning out of subrupture damage regime 204 and into incomplete tear regime 206. As another example, because transition curve 216 represents cycles and stress levels for undamaged soft tissue to transition out of incomplete tear damage regime 206, a given soft tissue may pass through no damage regime 202, subrupture damage regime 214, and incomplete tear regime 206 before transitioning out of incomplete tear damage regime 206 to a complete tear.

The damage regimes disclosed herein are advantageous for a variety of reasons. For example, individuals in no damage regime 202 or subrupture damage regime 204 typically suffer no symptoms, e.g., no pain, even though their soft tissue may have sustained subrupture damage. Some individuals in incomplete damage regime 206 suffer no symptoms despite having incurred incomplete tear of their soft tissue. Examples can predict damage based on the regimes even though an individual that has sustained the damage may be unaware of the damage. Examples can utilize the damage regimes to prevent injuries from becoming symptomatic. Examples can utilize the damage regimes to determine rest periods intended to prevent further damage and encourage healing. These and other advantages of the test regimes and other features are described in detail herein.

Figure 3:
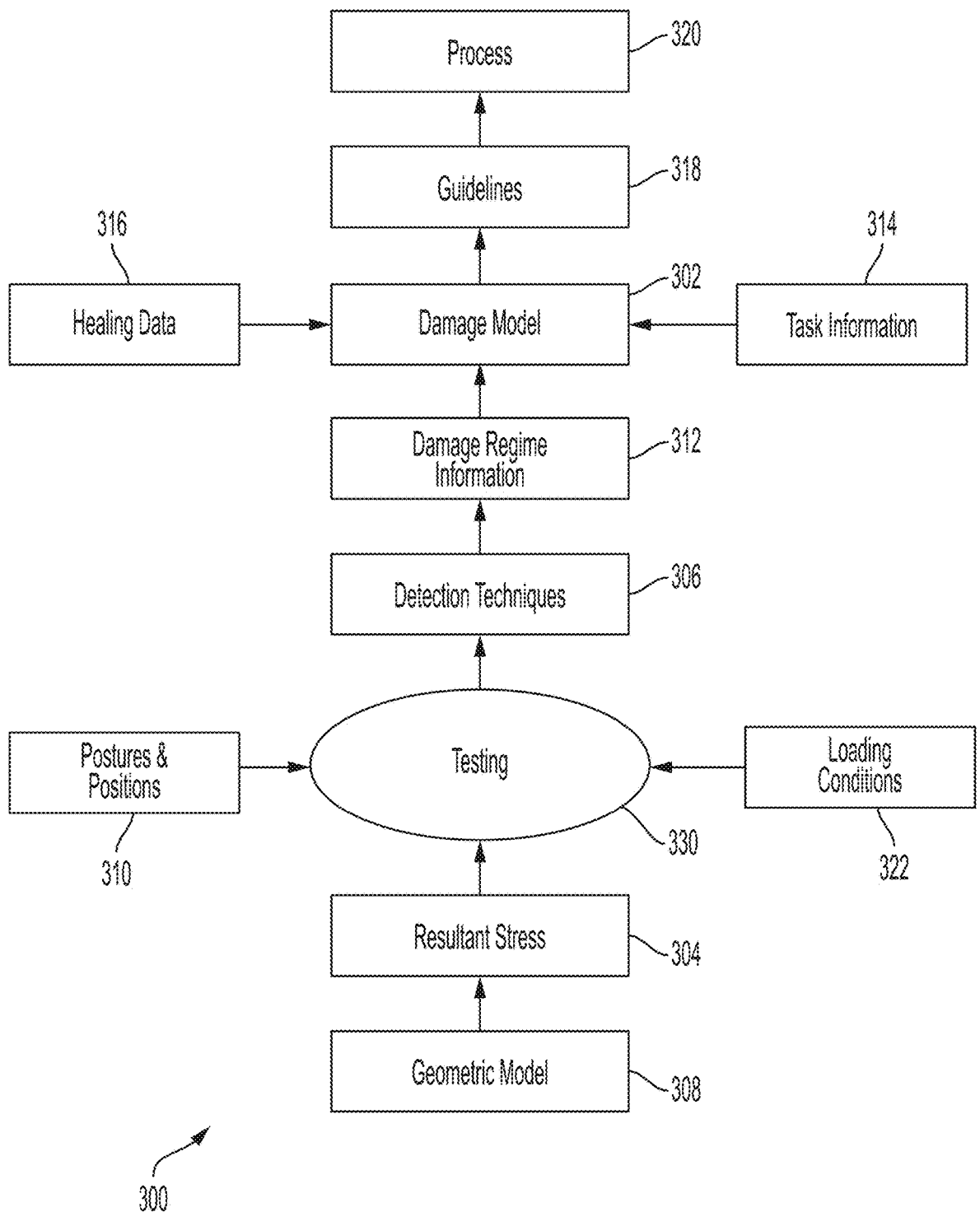
FIG. 3 is a schematic hybrid diagram that depicts example system elements and method steps according to various examples.

FIG. 3 is a schematic hybrid diagram 300 that depicts example system elements and method steps according to various examples. Central to diagram 300 is testing 330. In general, testing 330 utilizes detection techniques 306 to determine whether individuals of a plurality of test subjects have transitioned out of a damage regime, e.g., out of no damage regime 202, out of subrupture damage regime 204, or out of incomplete tear regime 206. Such transitions, together with the associated loading conditions 322, positions and postures 310, and resultant stress 304, provide damage regime information 312, which is used to generate damage model 302. Damage model 302, which also incorporates healing data 316 and task information 314, may be used to generate guidelines 318, which may be implemented in process 320. When implemented in process 320, guidelines 318 may prevent, mitigate, or ameliorate injuries in the individuals performing process 320. These and other features are described in detail presently.

Testing 330 includes selecting a plurality of test subjects and performing movements having known properties to determine transitions out of various damage regimes. The test subjects may be human, animal, or synthetic (e.g., polymer surrogate material). The test subjects may be living or deceased, e.g., a cadaver. A statistically significant number of test subjects may be selected. According to some examples, at least 50 test subjects are selected. According to some examples, at least 100 test subjects are selected. The movements may be selected to be similar or identical to movements that are performed as part of process 320.

Testing 330 can include specifying loading conditions 322 of the movement. Example loading conditions include compression, shear, and tension. In general, there may be certain muscle/tendon structures having a relationship or correlation between the tissues that participate in the tasks. Therefore, the movement can be performed under one or multiple loading conditions.

Loading conditions can be related to positions and postures 310. "Posture" can refer to qualitative characterizations of the subject's body or part thereof. A posture can be defined in terms of relative positions of identified landmarks. For example, a particular posture referred to as "overhead work" can be defined as the situation when the subject's elbow is above the subject's shoulder. In general, a posture can define a body position in a qualitative way, such that it can be observed and compared to another observation or position. A position of a subject (or a portion of the subject's body) can be determined by observational study by an ergonomist or industrial engineer according to various examples. "Position" can refer to quantitative characterization of the subject's body or part thereof. For example, a position can be defined using measurement equipment, with units like length, angle, or x-y-z coordinates. Thus, a tendon position can be defined at coordinates, e.g., (0 cm, 5 cm, 1 cm), where origin (0 cm, 0 cm, 0 cm) is where the tendon attaches to the humerus, and the coordinates correspond to positions in the following planes as follows: x=saggital, y=transverse, and z=coronal.

Both position and posture of a subject (or a portion of the subject's body) can be determined through the use of motion tracking according to various examples. Such motion tracking can be performed by a motion tracking system that uses optical (e.g., infrared), sonic (e.g., ultrasonic), or radiofrequency (RF) transmitters or reflectors and corresponding sensors to continuously track the subject's limb or other body portion in three-dimensional space. Such sensors can be distributed in three-dimensions about a space in which the subject is positioned, and the transmitters/reflectors may be attached to the subject; this description represents "outside-in" tracking. Alternately, according to some examples, the motion tracking system may utilize "inside out" tracking, in which the sensors are placed on the subject, and the transmitters/reflectors are distributed about the space where the movement is performed. Some examples utilize motion tracking that does not include transmitters or reflectors. Such examples can track motion using one or more video cameras and, for example, computer vision analysis. Some examples utilize accelerometers (e.g., Inertial Measurement Unit Sensors, Acceleration Measurement Unit) attached to the subject. Regardless as to the type, the motion tracking system may determine posture by matching determined locations of the subject's body or part thereof to data associated with various positions. The motion tracking system can determine positions by specifically measuring distances in relation to the subject's movements.

Testing 330 further includes determining resultant stress 304 on the soft tissue due to each cycle of the movement. Resultant stress 304 can be determined by first determining resultant force. The term "resultant force" may refer to a combination of the forces acting on soft tissue during work, including posture, position, vibration, tool weight, force vector applied at the hand, arm weight, etc. Tensile force is relevant to shoulders, but other soft tissue, such as intervertebral discs, can experience compressive force. Other types of soft tissue can experience both compressive and tensile forces. The force can be determined by observation and empirical measurements, as described in detail herein, or by using an estimation and/or modeling technique, such as finite element modeling (FEM) and/or electromyography (EMG). The force can be express in Newtons, and the stress can be expressed in Megapascals (MPa), for example.

According to some examples, the resultant stress 304 of a single cycle of the movement can be determined by dividing the resultant force for the cycle by the area of the affected soft tissue cross-sectional. Thus, determining resultant stress 304 can include determining the cross-sectional area of the affected soft tissue. Examples may determine such an area using a variety of techniques.

Some examples determine the cross-sectional area of the affected soft tissue based on a geometric model 308. Such a model can approximate the shape of the cross-sectional area as a circle, an oval, or a different two-dimensional geometric shape. The geometric model 308 can be based on past research as to the shape of various soft tissue cross-sections. Further, the geometric model 308 can account for age, gender, size, and other particular demographics of the subject based on past empirical measurements performed on individuals with similar characteristics. Thus, the soft tissue cross-sectional area for the geometric model 308 can be based on average cross-sectional areas for various soft tissue types, specific cross-sectional areas per demographic combination (e.g., sex, age, gender, height, weight, etc.), or a combination of such data.

Some examples determine the cross-sectional area of the affected soft tissue through the use of ultrasound. For example, longitudinal ultrasound using a longitudinal ultrasound device may be used to directly measure the dimensions of the cross-sectional area. Alternately, or in addition, longitudinal ultrasound can be used to measure Young's modulus for the soft tissue. The stress may then be computed from the measured Young's modulus. Whether cross-sectional area or Young's modulus, the measurements can be performed for a variety of positions and postures 310. This assists in more accurate estimates of stress, as soft tissue such as tendons typically has changing properties as position changes, e.g., as tendons elongate, they tend to become stiffer.

Alternately, or in addition, according to some examples, shear wave ultrasound using a shear wave ultrasound device can be used to measure resultant stress 304. For example, shear wave ultrasound may be used to measure a shear modulus. The stress may then be computed from the measured shear modulus. Again, these measurements can be computed for a variety of positions and postures 310.

Once resultant stress 304 is determined and loading conditions 322, as affected by positions and postures 310, are specified, the subjects can perform the movement repeatedly and be tested for transition out of a damage regime using detecting techniques 306 in order to obtain damage regime information 312. In general, damage regime information 312 can be used to generate associations, such as transition curves 212, 214, and 216, as shown and described above in reference to FIG. 2. A plurality of associations may be generated, e.g., for each of a plurality of loading conditions, transition curves corresponding to transition curves 212, 214, and 216 may be generated. Thus, the detection techniques can be used to detect soft tissue disorganization, tears, including microscopic tears, subrupture damage, incomplete tear damage, and complete tear damage. Detection techniques 306 can be deployed periodically during, before, and/or after one or more test sessions. According to various examples, detection techniques 306 can be used after every increment of a set number of cycles of a movement, e.g., every 10 movements, every 50 movements, every 100 movements, every 250 movements, every 500 movements, every 750 movements, or every 1000 movements. Any of a variety of detection techniques 306 may be used. According to some examples, noninvasive techniques are used for detection techniques 306.

Detection techniques 306 can include ultrasound speckle tracking. Ultrasound speckle tracking can be used to measure strain, such as regional strain. To do so, some examples obtain a reference ultrasound image of the soft tissue and note any distinct features, such as speckles or other imperfections. Physical speckles (e.g., brass or gold beads) can also be inserted into the soft tissue. Then, the soft tissue can undergo a movement, and movement of one or more speckles are tracked, e.g., using ultrasound. The distance the speckles move provides a quantification of strain in the soft tissue. Further, ultrasound speckle tracking can be used to detect soft tissue disorganization by noting how speckles shift after repeated movements. Note that ultrasound speckle tracking can be performed non-invasively in vivo.

Detection techniques 306 can include ultrasound tissue characterization. According to some implementations of ultrasound tissue characterization, the soft tissue, such as a tendon, is held in a fixed position while a probe is translated across automatically while taking images in the transverse direction. These images produce echo patterns. The echo patterns may be classified into distinct categories, such as highly stable (I), medium stable (II), highly variable (III), and constantly low intensity (IV). The proportion of each echo pattern is significantly different when a tendon is symptomatic versus asymptomatic. One or more of these categories, or one or more relative proportions of these categories, can correlate with a transition out of a particular damage regime. Further, ultrasound tissue characterization is reliable, in that it has been shown to have consistent intraobserver reporting of the same soft tissue. Thus, ultrasound tissue characterization can provide a technique for assessing soft tissue, in real time, for degradation. Note that ultrasound tissue characterization may be performed non-invasively in vivo.

Some examples use one or multiple forms of ultrasound elastography as detection technique(s) 306. In general, either or both of ultrasound shear wave elastography or ultrasound compressive elastography can be used to detect a damage regime transition. According to some examples, both can be used to exploit the relative orientations of the ultrasound waves. Some soft tissue features can be essentially one-dimensional or two-dimensional. Using multiple forms of ultrasound elastography with different wave orientations may reveal features that would be difficult to detect using a single ultrasound elastography technique, e.g., because of the orientation of the feature relative to the orientation of the ultrasound waves. For example, a tear can be essentially one-dimensional or two-dimensional, and can therefore be difficult to detect using ultrasound with waves that are perpendicular to the plane(s) of the tear. Further, multiple forms of ultrasound elastography can be particularly beneficial for detecting soft tissue disorganization, which can scatter ultrasound waves in multiple directions. Regarding ultrasound shear wave elastography, a probe can produce a shear wave that propagates through the tendon, and the velocity of wave propagation can then be used to estimate the modulus of elasticity (tendon stiffness), with higher velocities seen in stiffer tissues. The modulus of elasticity can be used to determine strain, or can provide damage regime information in the form of a slope of a transition curve at a point, e.g., a calculus derivative of a transition curve at a point. Regarding ultrasound compressive elastography, a probe can be used to compress the tendon, e.g., for comparison against adipose tissue. Ultrasound compressive elastography is particularly suitable because it has very good intra and inter operator reliability. Note that both ultrasound shear wave elastography and ultrasound compressive elastography may be performed non-invasively in vivo.

Some examples use cross-sectional microscopy, such as collagen disorganization characterization, as one of detection techniques 306. According to some such examples, a cadaver (or animal) tendon or other soft tissue is prepared, including adding tracking speckles, e.g., brass or gold beads, to various locations for tracking purposes. The soft tissue is then tested on a test apparatus, where stress is a known quantity applied by the apparatus. The change in distance of the brass beads directly correlates to strain. Further, polarized photographs may be taken to best assess fiber direction. Operators of examples may quantify the change in orientation of the fibers in a sample by looking at pixel intensity, e.g., by quantifying disorganization as circular variance based on the variety of fiber orientations.

Other forms of detection techniques 306 include empirical measurements of materials science properties of soft tissue based on Computerized Axial Tomography (CAT) scan data, Magnetic Resonance Imaging (MRI) scan data, destructive testing data, molecular dynamic modeling (MDM) data, publication data, and/or any combination thereof.

In sum, detection techniques 306 may detect whether a particular soft tissue in a test subject has undergone a damage regime transitions. Detection techniques 306 may be invasive or non-invasive and may be performed in vivo or otherwise. The damage regime transition information obtained using detection techniques 306 can be used to generate damage regime information 312 as described presently.

Damage regime information 312 can be in the form of separate sets of damage regime information for each movement type, damage regime, and loading condition. In this manner, a plurality of associations may be generated. Each set of damage regime information can quantify a number of cycles of a specified movement type at a given stress (or strain) for the soft tissue to transition out of the respective damage regime. For example, a first damage regime information can quantify a number of cycles per given stress for the soft tissue to transition out of the first damage regime; a second damage regime information can quantify a number of cycles per given stress for the soft tissue to transition out of the second damage regime, and, for examples that include a third damage regime, a third damage regime information can quantify a number of cycles per given stress for the soft tissue to transition out of the third damage regime.

Each damage regime information for a particular movement type, damage regime, and loading condition can be in the form of an association, e.g., a curve, quantifying a number of cycles at a given stress for the soft tissue to transition out of the respective damage regime, e.g., with stress (or strain) as an independent variable and cycles as a dependent variable. For example, each information can be in the form of a curve according to various examples. When stored in a computer, such information can be in the form of a set of ordered pairs (S, N), where S represents stress (or strain) and N represents a number of cycles to transition out of the respective regime.

In general, damage regime information 312 can be, or may be used to derive, data as shown described above in reference to FIG. 2. According to various examples, the first damage regime can be a no-damage regime, the second damage regime can be a subrupture damage regime, and, for examples that include it, the third damage regime can be a partial tear regime. (Note that any combination of at least two damage regimes can be used according to various examples, not limited to those explicitly set forth presently.) Examples that incorporate either or both of the no-damage regime and the subrupture regime can predict damage to subject soft tissue prior to the subject realizing that damage has occurred. For example, soft tissue within these regimes can be damaged, but cause no pain or discomfort to the subject.

Damage regime information 312 may be stored in the form of computer files, e.g., in tab-delimited or comma-separated value (CSV) format. Damage regime information 312 can be obtained during use of an example by being read from persistent electronic storage by a computer, or by the data being entered into file format and stored in the computer, by way of non-limiting examples.

Damage model 302 can be implemented using a finite element method to fit the data obtained through testing 330 to damage regime curves. Damage model 302 can utilize the curves represented by, or generated from, damage regime information 312 to determine and/or predict damage. Damage model 302 can use task information 314, which indicates the repetitive injury exposure that the subject has (or will) incurred in performing a task, as compared to curves represented by or derived from damage regime information 312 to determine whether soft tissue damage has or will occur. Thus, model 302 determines whether the task described by task information 314 will cause (or has already caused) the soft tissue to transition into a different damage regime.

Task information 314 can represent the exposure that a subject might accrue (or has accrued) over the course of completing one task that forms part of an overall process, e.g., a manufacturing process. The exposure can be represented in the form of any, or a combination, of: a resultant stress, a number of cycles, an associated time interval in which the cycles are performed, and/or a description of a movement for each cycle, e.g., in narrative form. According to some examples, task information 314 can account for multiple types of movements. Task information 314 can be in the form of computer files, e.g., in tab-delimited or comma-separated value (CSV) format. Task information 314 can be obtained by being read from persistent electronic storage by a computer, or by the data being entered into file format and stored in the computer, by way of non-limiting examples.

In order to evaluate task information 314 in light of the damage estimations and predictions of model 302, the resultant stress of each cycle of a movement described in task information 314 under a plurality of loading conditions may be determined. This resultant stress data can be included with task information 314. Based on the resultant stress, the damage model 302 can determine whether damage has or will occur.

The determination of whether damage has occurred or will occur can utilize material science properties of the soft tissue. According to some examples, the determination can be performed as follows. For convenience of exposition, the determination is described in terms of prediction; however, the determination may be equally used to detect damage already incurred. First, the resultant stress per cycle of movement may be determined. Second, the cumulative resultant stress can be computed by multiplying the resultant stress for a particular cycle by the number of cycles performed or to be performed, as represented in the task information 314. Third, the cumulative resultant stress can be compared to the damage regime information 312. For example, for a cumulative stress that represents R cycles each at a stress level of S, the cumulative stress $\Sigma S$ can be considered an independent variable in the information representing the current damage regime of the soft tissue, and the corresponding dependent variable R' in terms of a number of cycles for transition out of the damage regime can be identified. Fourth, the number of cycles R' of the identified dependent variable can be compared with the number R of cycles set forth in the task information 314. If the former is greater than the latter, then the soft tissue is predicted to remain in its current damage regime, and therefore no additional damage is predicted. If, however, the former is less than or equal to the latter, then the soft tissue may be predicted to transition out of the respective damage regime. In that case, the soft tissue is predicted to undergo damage. Thus, the soft tissue is predicted to undergo damage when the number of cycles R set forth in the task information 314 for stress level S meets or exceeds the number of cycles R' corresponding to S per the information characterizing the current damage regime for transition out of the current damage regime as set forth in the damage regime information 312.

This process can be performed for multiple tasks as represented in the task information 314. For example, the products of the cycles and stress levels can be summed. This sum can be compared to the damage regime information 312. If the sum is greater, then the soft tissue may be predicted to undergo damage, that is, transition out of a damage regime. Otherwise, the soft tissue may be predicted to remain in the current damage regime.

An example usage of model 302 to predict damage (or ascertain if damage has already occurred) is set forth presently. Per this example, the task information 314 includes: Task A at 50 cycles, Task B at 500 cycles, and task C at 5000 cycles. The resultant force for a single cycle of each task may be set forth in the task information 314 or determined as part of computing the resultant stress as, for example: Task A force=150 N, Task B force: 100 N, and Task C force: 50 N, where the units are Newtons.

Stress is force divided by cross-sectional area of the soft tissue, which can be determined from ultrasound and/or a geometric model 308. For purposes of this example, the cross-sectional area is 50 $mm^2$. Thus, Task A stress=3 MPa, Task B stress=2 MPa, and Task C stress=1 Mpa per cycle, where the units are megapascals Per this example, the damage regime information may indicate a transition out of the no-damage regime occurs at 1000 cycles at 4 MPa (this is one point along the curve).

The stress from the tasks can be compared to the no-damage regime limit as 3 MPa*50+2 MPA*500+1 MPa*5000>4 MPa*1000. This means that the no-damage regime is exceeded. Thus, the next regime (e.g., subrupture) would need to be calculated to and may be the next one after, and so on up to complete failure of the soft tissue, that is, up to transition out of the incomplete tear regime.

Healing data 316 can be applied by damage model 302, e.g., if multiple tasks are combined with rest periods in between (e.g., a percentage reduction in exposures, moving to a lower point on the curve, etc.). While soft tissue such as tendons behave like materials with predictable fatigue failure at given stress levels and cycles, they are also able to self-repair. When people are engaged in physical activity, the effects of repeated stress on soft tissues result in small fissures, referred to herein as microtrauma or subruptures. Subruptures themselves are not harmful to the body because the body will repair itself to become stronger given a sufficient recovery period; this is the underlying benefit of exercise. Thus, a recovery period may be on the order of hours, days, or possibly weeks. With insufficient recovery period, the tendon becomes damaged and eventually an injury will occur. Thus, model 302 may take into account recovery periods in which the soft tissue self-repairs. Accordingly, model 302 can also be based on healing data 316. Healing data 316 can include data representing healing rates of various soft tissues. For example, healing data 316 can include healing rates of each of a variety of tendons. Further, healing data 316 can be arranged according to demographic information. For example, healing data can include healing rates of particular soft tissue types according to various age groups, e.g., 18-30, 30-40, 40-50, and 50-60 years old. Further, healing data 316 can be specific to each damage regime, e.g., specific to soft tissue with no damage, specific to soft tissue with subrupture damage, and specific to soft tissue with partial tear damage. That is, each tissue damage type can have associated specific healing data 316.

Healing data 316 can be applied in model 302 in a variety of ways. In some examples, model 302 applies healing data 316 by reducing a count of a number of cycles that the soft tissue has undergone. The cycle count may be reduced by an amount corresponding to the recovery period. Thus, in some examples, healing data 316 associates healing time with cycle reductions.

Healing data 316 may be obtained using a variety of information sources and techniques. According to some examples, healing data 316 is determined by comparing soft tissue damage in a live human or animal subject at a first time to damage of the same soft tissue at a second, later time, after which healing has occurred. Noninvasive detection techniques, e.g., as described herein in reference to detection techniques 306, may be used. According to some examples, if the tissue has transitioned damage regimes downward, e.g., from partial tear damage to subrupture damage, or from subrupture damage to no damage, then a count of cycles can be reduced accordingly. According to some examples, healing data 316 is determined by comparing cadaver soft tissue with live subject soft tissue. These soft tissues can be compared subsequent to both being subjected to the same movement and cycles and after a time interval has elapsed. A difference between damage of the soft tissues is indicative of healing during the elapsed time interval. If the difference reflects a difference in damage regimes, between partial tear damage and subrupture damage, or between subrupture damage and no damage, then a count of cycles can be reduced accordingly.

The example calculations presented above provide a point solution (just one number and one answer) for one iteration. For better model fidelity, this iteration can be run a number of times, sampling from distributions of, for example, soft tissue geometries, the force on the soft tissue, and potentially variation in the cycles. For example, this can be a model run multiple times with slightly different probabilistic inputs, similar to a Monte Carlo simulation. This provides an output of the risk with some boundaries or bands around it (e.g., a 95% confidence interval, etc.). Optionally, other variables, such as demographics are also added to the model.

Based on the damage model 302, examples can produce guidelines 318 for avoiding or ameliorating soft tissue damage. As used herein, the term "guideline" embraces a recommended set of evidence-based limits on one or more of force (e.g., vibration, tool weight, force vector applied at the hand, arm weight, etc.), posture, position, frequency, duration and/or recovery, intended to safeguard human tissue material from the risk of injury due to soft tissue damage during human activity such a manufacturing or other processes. In general, each guideline can reduce a number of cycles and/or an amount of stress corresponding to actions in the task information 314. Each guideline can thus specify a posture or position of the soft tissue, and limits on any of: a number of cycles of a given movement of the soft tissue, a force applied to the soft tissue, a duration of maintaining a given posture or position of the soft tissue, a duration of a cycle of a given movement of the soft tissue, a duration of a given force applied to the soft tissue, or a combination thereof. Such parameters can be specified such that the calculations described above predict no damage. The parameters so specified can form all or part of a guideline.

In general, the guidelines 318 can reduce the stress on the soft tissue by reducing the force on the soft tissue in any of a number of ways. The force on the soft tissue can be a resultant force on the soft tissue, the force being the result of posture (or position), weight (e.g., of the arm and/or holding an object such as a tool), applied force vector (e.g., pushing at the hand), vibration (from holding a vibrating object such as a hand tool), etc. According to some examples, the force is reduced by placing a limitation on any of the above parameters.

The force on the soft tissue can alternately, or in addition, be reduced placing a limitation on the position and/or posture of the subject's body or portion thereof, thus affecting a position and/or posture of the soft tissue. According to various examples, the guideline can include a limitation on at least one of a position of the soft tissue, and/or a posture of the soft tissue.

Alternately, or in addition, the force on the soft tissue can be reduced by placing a limitation on a temporal duration of a movement, position, or posture. That is, the guideline can place a limitation on any, or a combination, of: a duration of maintaining a given posture of the soft tissue, a duration of maintaining a given position of the soft tissue, a duration of a cycle of a given movement of the soft tissue, and/or a duration of a given force applied to the soft tissue.

According to some examples, the guidelines 318 can include imposed rest periods. Such examples can utilize healing data 316 to counteract micro-damage or macro-damage. The rest periods can represent sufficient time for such healing processes to counteract any accumulated damage.

Once produced, the guidelines 318 can be output and utilized in a process 320, such as a manufacturing process. The guidelines 318 can be output in any of a variety of forms. According to some examples, the guidelines are output in narrative form using pre-generated narrative templates. For example, if the computations indicate that the number of cycles should be reduced from 1000 to 725, the guideline can populate these numbers into a template that reads in part, "The number of cycles for action X should be reduced from Y to Z," where X, is replaced with a description of the action, Y is replaced by 1000, and Z is replaced by 725. The formatted guidelines can be output by displaying on a computer monitor, by email, or by any other techniques that provide the information to a person or process.

Implementing the guidelines in a process can include providing the guidelines to workers on an assembly line, for examples in which the process is a manufacturing process. The workers can then alter their tasks accordingly. For examples in which the process is an athletic training process, the guidelines can be provided to the trainer, who alters the athlete's training plan accordingly. Further, the guidelines can be used to design production systems, products, work tasks, training plans, etc.

Figure 4:
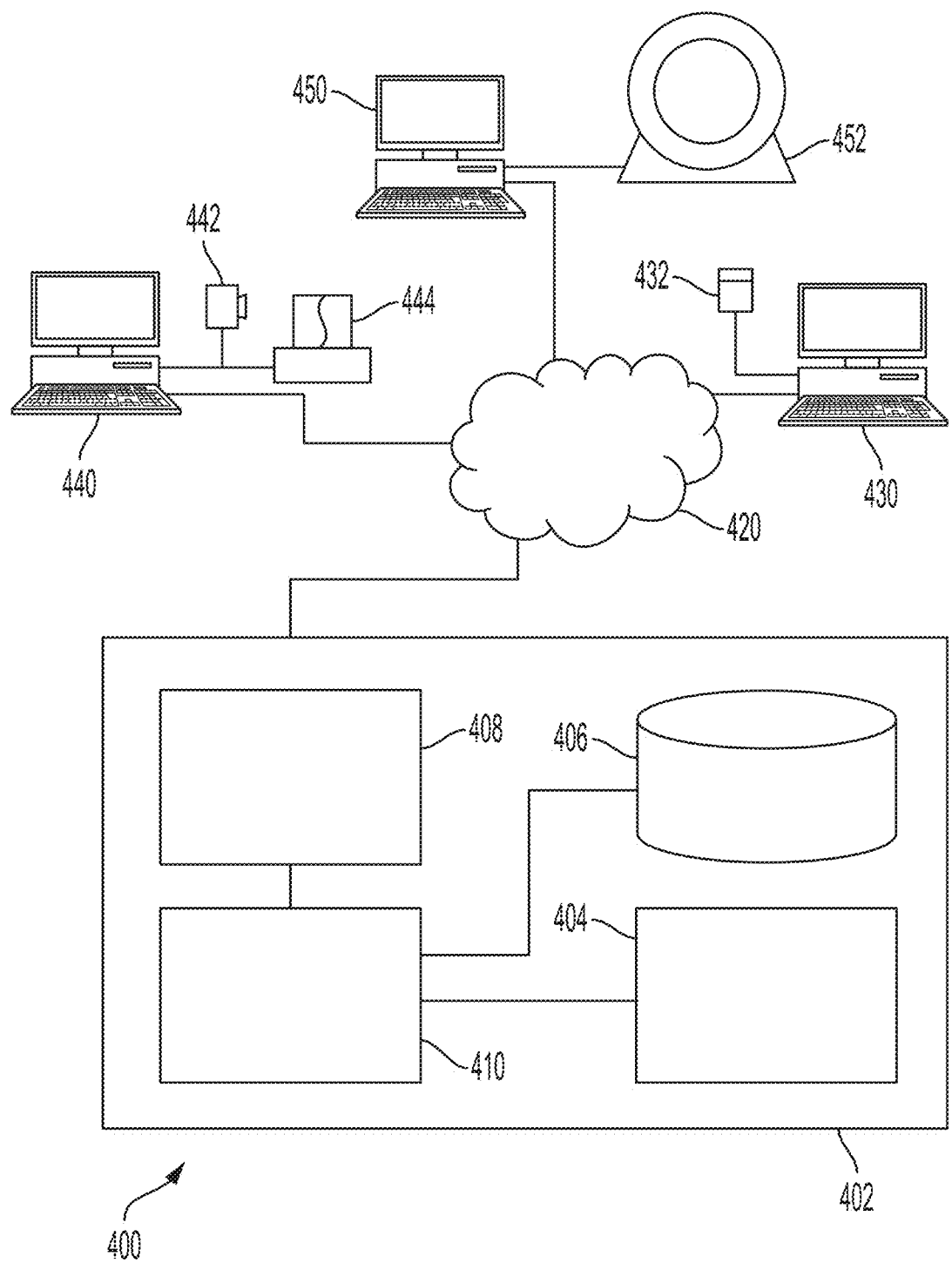
FIG. 4 is a schematic diagram of a system for mitigating injury in performing a process according to various examples.

FIG. 4 is a schematic diagram of a system for mitigating injury in performing a process according to various examples. For example, FIG. 4 illustrates various hardware, software, and other resources that can be used in implementations of method 500 as shown and described below in reference to FIG. 5.

System 400 includes computer 402. Computer 402 can be a desktop computer, a laptop computer, can be incorporated in one or more servers, clusters, or other computers or hardware resources, or can be implemented using cloud-based resources. Computer 402 includes volatile memory 404 and persistent memory 406, the latter of which can store computer-readable instructions, that, when executed by electronic processor 410, configure computer 402 to at least partially perform methods, e.g., method 500, as shown and described herein.

System 400 further includes instrumentation to perform the detection techniques disclosed herein, e.g., detection techniques 306.

For example, system 400 includes ultrasound device 430 (including ultrasound transducer 432). Ultrasound device 430 may be a shear wave ultrasound device or a longitudinal ultrasound device, for example. According to some examples, both types of ultrasound device may be included in system 400. Ultrasound device 430 may be used to perform any, or any combination, or ultrasound speckle tracking, ultrasound tissue characterization, and/or ultrasound elastography, as described herein, e.g., in reference to detection techniques 306 of FIG. 3.

As another example, system 400 includes collagen disorganization characterization system 440, including camera 442 and test apparatus 444. Test apparatus 444 may hold soft tissue and apply a known stress, and camera 442 may capture polarized images of the soft tissue, as described herein, e.g., in reference to detection techniques 306 of FIG. 3.

As yet another example, system 400 includes three-dimensional (3D) imaging device 450, including 3D imaging scanner 452. The 3D imagining scanner 452 may be a Computerized Axial Tomography (CAT) scanner or a Magnetic Resonance Imaging (MRI) scanner. According to some examples, both types of scanner are included in system 400. The 3D imaging device may capture images of soft tissue as described herein, e.g., in reference to detection techniques 306 of FIG. 3.

Computer 402 is communicatively coupled to the ultrasound device 430, the collagen disorganization characterization system 440, and the 3D imaging device 450 via a network interface 408, such as an Ethernet or wireless data connection, which in turn can communicate via one or more networks 420, such as the Internet or other public or private networks. According to some examples, data from the ultrasound device 430, the collagen disorganization characterization system 440, and/or the 3D imaging device 450 is stored persistently on a computer communicatively coupled to, and retrieved by, computer 402 via network 420. Computer 402 also includes a monitor, on which generated guidelines may be displayed. Other configurations of system 400, associated network connections, and other hardware, software, and service resources are possible.

Figure 5:
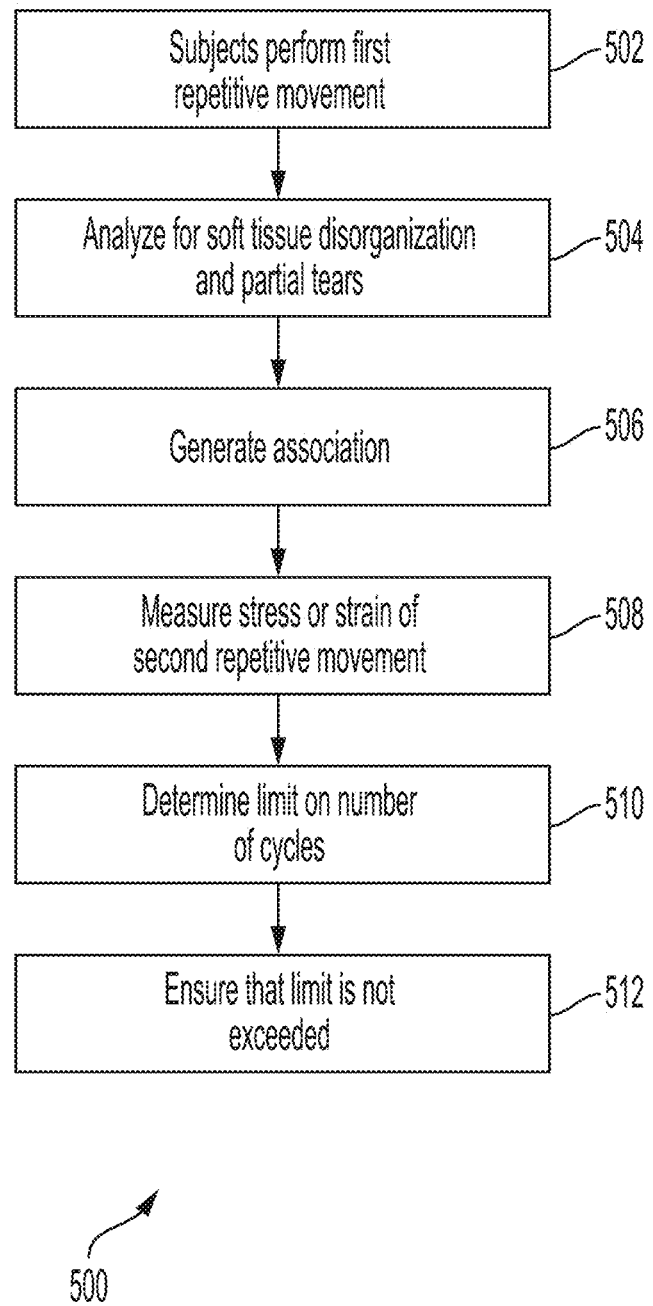
FIG. 5 is a flowchart depicting an example method of mitigating injury in performing a process according to various examples.

FIG. 5 is a flowchart depicting an example method 500 of mitigating injury in performing a process according to various examples. For example, each worker can have one or more tasks that form part of the manufacturing process, e.g., on an assembly line. The tasks for each worker can be modified by the one or more guidelines produced by method 500. Alternately, method 500 can be used to ameliorate repetitive stress injuries of an athlete executing a training program, for example. The athlete can have one or more exercises that form part of the training program. The exercises can be modified by the one or more guidelines produced by method 500. In general, method 500 can be practiced to ameliorate repetitive stress injuries in any type of process that includes repetitive movements by a person, not limited to manufacturing or athletic processes.

Method 500 can be used to ameliorate injuries to any of a variety of soft tissues. For example, method 500 can mitigate or ameliorate injuries by providing data that can be used to drive changes through the ability to characterize actual damage rather than relying on theoretical or epidemiological information. According to some examples, method 500 can be used to ameliorate injuries to tendons or tendon complexes. Examples of such tendons and tendon complexes are presented herein. Alternately, method 500 can be used to ameliorate injuries to connective tissue or musculoskeletal soft tissue. In general, non-limiting examples of soft tissues for which examples can be implemented include tendons, tendon complexes, intervertebral (spinal) discs, and ligaments.

Method 500 may be implemented using system 400 as shown and described below in reference to FIG. 4. Method 500 includes extra-computer actions that provide improvements in the field of industrial hygiene. Such actions include, for example, obtaining physical parameters using, for example, one or more ultrasound devices, e.g., ultrasound device 430, one or more soft tissue disorganization characterization systems, e.g., collagen disorganization characterization system 440, and/or one or more 3D imaging devices, e.g., 3D imaging device 450.

At 502, method 500 includes performing, by a plurality of subjects, a first repetitive movement with at least one of a specified stress per cycle or a specified strain per cycle. The plurality of subjects may include test subjects as described herein, e.g., living humans, cadavers, living or deceased animals, or a synthetic proxies. Actions of 502 may include actions described herein in reference to testing 330, as shown and described herein in reference to FIG. 3, for example.

At 504, method 500 includes analyzing for a presence of at least one of soft tissue disorganization or partially torn soft tissue in each of the subjects. The analyzing can include usage of any of the detection techniques disclosed herein, e.g., detection techniques 306, which may be implemented using detection instrumentation as shown and described herein in reference to FIG. 4.

At 506, method 500 includes generating an association, based on the analyzing, where the association relates one of stress or strain to a number of cycles that cause at least one of: a transition to subrupture damaged tissue, or a transition to incomplete tear damaged tissue. The actions of 502 can include fitting a model to damage regime information obtained per the performing of 502 and the analyzing of 504. In general, the actions of 502 can include actions as shown and described in reference to damage model 302 of FIG. 3.

At 508, method 500 includes measuring at least one of a stress per cycle or a strain per cycle for a second repetitive movement comprising the process. The second repetitive movement can be a movement that forms part of a process such as a manufacturing process, for example. The actions of 508 can include, for example, actions as shown and described in reference to task information 314 of FIG. 3.

At 510, method 500 includes determining, based on the association, a limit on a number of cycles of the second repetitive movement intended to avoid at least one of: a transition to subrupture damaged soft tissue, or a transition to incomplete tear damage tissue. The actions of 510 may include actions as shown and described herein in reference to guidelines 318 of FIG. 3.

At 512, method 500 includes performing the second repetitive movement as part of the process, where the performing the second repetitive movement includes ensuring that no individual subject exceeds the limit on the number of cycles of the second repetitive movement. The actions of 512 can include implementing guidelines in a process, e.g., as shown and described herein in reference to guidelines 318 of FIG. 3.

At 504, method 500 fits a soft tissue damage model based on the physical parameters of 502. Fitting the model can include adapting a model to the physical parameters of 502. The soft tissue damage model can be based on a Finite Element Method (FEM) simulation of the soft tissue. The soft tissue damage model can account for at least two damage regimes, e.g., at least two of a no-damage regime, a subrupture regime, and a tear propagation regime, as shown and described above in reference to FIG. 1.

At 506, method 500 ameliorates injury in a subject performing the process under consideration. To do so, method 500 may include developing guidelines and implementing the guidelines in the process. The guidelines can include a limitation on at least one of: a posture of the soft tissue, a number of cycles of a given movement of the soft tissue, a force applied to the soft tissue, a duration of maintaining a given posture of the soft tissue, a duration of a cycle of a given movement of the soft tissue, or a duration of a given force applied to the soft tissue, as shown and described above in reference to FIG. 1. The guidelines may be implemented by providing the guidelines to workers on an assembly line, for example. Consequently, by following the guidelines, the risk of soft tissue injury to the subject due to repetitive stress injury is ameliorated.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A method of performing a process, the method comprising:
    performing, by a plurality of subjects, a first repetitive movement with at least one of a specified stress per cycle or a specified strain per cycle;
    analyzing for a presence of at least one of soft tissue disorganization or partially torn soft tissue in each of the plurality of subjects;
    generating an association, based on the analyzing, wherein the association relates one of stress or strain to a number of cycles that cause at least one of: a transition to subrupture damaged tissue, or a transition to incomplete tear damaged tissue;
    measuring at least one of a stress per cycle or a strain per cycle for a second repetitive movement comprising the process;
    determining, based on the association, a limit on a number of cycles of the second repetitive movement intended to avoid at least one of: a transition to subrupture damaged soft tissue, or a transition to incomplete tear damage tissue, wherein the determining the limit on the number of cycles of the second repetitive movement is further based on healing data for the soft tissue and at least one recovery period, wherein the healing data comprises data representing a difference in levels of soft tissue disorganization between a first soft tissue in a first subject measured using an invasive technique and a second soft tissue in a second subject measured using a non-invasive technique; and
    performing the second repetitive movement as part of the process, wherein the performing the second repetitive movement comprises ensuring that no individual exceeds the limit on the number of cycles of the second repetitive movement.

2. The method of claim 1, wherein the analyzing comprises analyzing using at least one non-invasive technique.

3. The method of claim 2, wherein the at least one non-invasive technique comprises at least one of: ultrasound speckle tracking imaging, ultrasound compression elastography, ultrasound strain elastography, shear wave elastography, magnetic resonance imaging, ultrasound tissue characterization, or a combination thereof.

4. The method of claim 1, wherein the association relates one of stress or strain to a number of cycles that cause a transition to subrupture damaged soft tissue.

5. The method of claim 1, wherein the association relates one of stress or strain to a number of cycles that cause a transition to incomplete tear damaged tissue.

6. The method of claim 1, further comprising:
    repeating, for each of a plurality of loading conditions, the performing the first repetitive movement, the analyzing, and the generating, wherein the plurality of loading conditions comprise at least two of: compression, shear, or tension, and wherein a plurality of associations comprising the association are produced; and
    determining a loading condition for the second repetitive movement;

wherein the association corresponds to the loading condition for the second repetitive movement.

7. The method of claim 1, wherein the association comprises a curve relating one of a stress or strain on a first axis to a number of cycles on a second axis.

8. The method of claim 1, wherein the process comprises a manufacturing process.

9. A system for performing a process, the system comprising at least one electronic processor that executes instructions to perform operations comprising:
    generating an association, based on analyzing for a presence of at least one of soft tissue disorganization or partially torn soft tissue in each of a plurality of subjects that perform a first repetitive movement with at least one of a specified stress per cycle or a specified strain per cycle, wherein the association relates one of stress or strain to a number of cycles that cause at least one of: a transition to subrupture damaged tissue, or a transition to incomplete tear damaged tissue; and
    determining, based on the association and a measurement of at least one of a stress per cycle or a strain per cycle for a second repetitive movement comprising the process, a limit on a number of cycles of the second repetitive movement intended to avoid at least one of: a transition to subrupture damaged soft tissue, or a transition to incomplete tear damage tissue, wherein the determining the limit on the number of cycles of the second repetitive movement is further based on healing data for the soft tissue and at least one recovery period, wherein the healing data comprises data representing a difference in levels of soft tissue disorganization between a first soft tissue in a first subject measured using an invasive technique and a second soft tissue in a second subject measured using a non-invasive technique;
    wherein the second repetitive movement is performed as part of the process while ensuring that no individual exceeds the limit on the number of cycles of the second repetitive movement.

10. The system of claim 9, wherein the generating the association is further based on analyzing for a presence of at least one of soft tissue disorganization or partially torn soft tissue using at least one non-invasive technique.

11. The system of claim 10, wherein the at least one non-invasive technique comprises at least one of: ultrasound speckle tracking imaging, ultrasound compression elastography, ultrasound strain elastography, shear wave elastography, magnetic resonance imaging, ultrasound tissue characterization, or a combination thereof.

12. The system of claim 9, wherein the association relates one of stress or strain to a number of cycles that cause a transition to subrupture damaged soft tissue.

13. The system of claim 9, wherein the association relates one of stress or strain to a number of cycles that cause a transition to incomplete tear damaged tissue.

14. The system of claim 9, wherein the operations further comprise:
    repeating, for each of a plurality of loading conditions, the generating and the determining, wherein the plurality of loading conditions comprise at least two of: compression, shear, or tension, and wherein a plurality of associations comprising the association are produced; and
    obtaining a loading condition for the second repetitive movement;
    wherein the association corresponds to the loading condition for the second repetitive movement.

15. The system of claim 9, wherein the association comprises a curve relating one of a stress or strain on a first axis to a number of cycles on a second axis.

16. The system of claim 9, wherein the process comprises a manufacturing process.

17. A method of performing a process, the method comprising:
    performing, by a plurality of subjects, a first repetitive movement with at least one of a specified stress per cycle or a specified strain per cycle;
    analyzing for a presence of at least one of soft tissue disorganization or partially torn soft tissue in each of the plurality of subjects;
    generating an association, based on the analyzing, wherein the association relates one of stress or strain to a number of cycles that cause at least one of: a transition to subrupture damaged tissue, or a transition to incomplete tear damaged tissue;
    measuring at least one of a stress per cycle or a strain per cycle for a second repetitive movement comprising the process;
    determining, based on the association, a limit on a number of cycles of the second repetitive movement intended to avoid at least one of: a transition to subrupture damaged soft tissue, or a transition to incomplete tear damage tissue;
    performing the second repetitive movement as part of the process, wherein the performing the second repetitive movement comprises ensuring that no individual exceeds the limit on the number of cycles of the second repetitive movement;
    repeating, for each of a plurality of loading conditions, the performing the first repetitive movement, the analyzing, and the generating, wherein the plurality of loading conditions comprise at least two of: compression, shear, or tension, and wherein a plurality of associations comprising the association are produced; and
    determining a loading condition for the second repetitive movement, wherein the association corresponds to the loading condition for the second repetitive movement.

18. The method of claim 17, wherein the analyzing comprises analyzing using at least one non-invasive technique.

19. A system for performing a process, the system comprising at least one electronic processor that executes instructions to perform operations comprising:
    generating an association, based on analyzing for a presence of at least one of soft tissue disorganization or partially torn soft tissue in each of a plurality of subjects that perform a first repetitive movement with at least one of a specified stress per cycle or a specified strain per cycle, wherein the association relates one of stress or strain to a number of cycles that cause at least one of: a transition to subrupture damaged tissue, or a transition to incomplete tear damaged tissue;
    determining, based on the association and a measurement of at least one of a stress per cycle or a strain per cycle for a second repetitive movement comprising the process, a limit on a number of cycles of the second repetitive movement intended to avoid at least one of: a transition to subrupture damaged soft tissue, or a transition to incomplete tear damage tissue;
    wherein the second repetitive movement is performed as part of the process while ensuring that no individual exceeds the limit on the number of cycles of the second repetitive movement;

repeating, for each of a plurality of loading conditions, the generating and the determining, wherein the plurality of loading conditions comprise at least two of: compression, shear, or tension, and wherein a plurality of associations comprising the association are produced; and obtaining a loading condition for the second repetitive movement, wherein the association corresponds to the loading condition for the second repetitive movement.

20. The system of claim 19, wherein the generating the association is further based on analyzing for a presence of at least one of soft tissue disorganization or partially torn soft tissue using at least one non-invasive technique.

* * * * *